Figure 3:
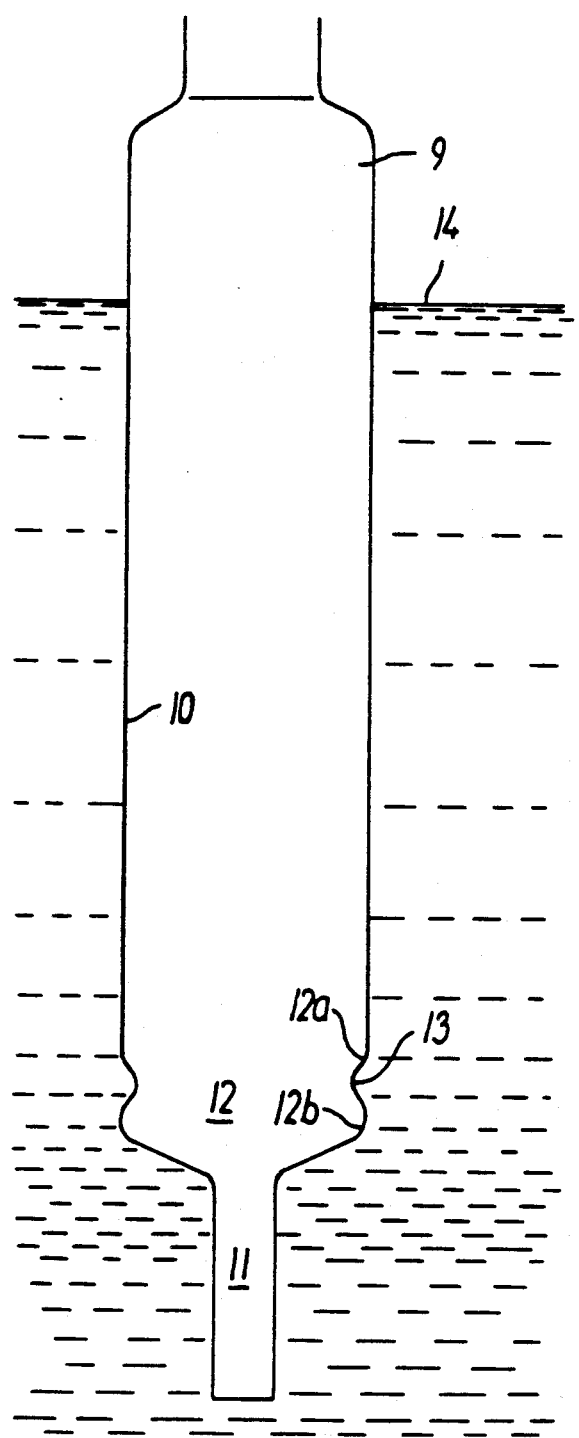

United States Patent [19]

Novak

[11] Patent Number: 5,059,190

[45] Date of Patent: Oct. 22, 1991

[54] EXTERNAL MALE URINARY CATHETER AND METHOD AND APPARATUS FOR MANUFACTURING SUCH A CATHETER

[75] Inventor: Julius Novak, Ringsted, Denmark

[73] Assignee: ColoPlast A/S, Denmark

[21] Appl. No.: 502,180

[22] Filed: Mar. 30, 1990

[30] Foreign Application Priority Data

Mar. 31, 1989 [GB] United Kingdom ................. 8907253

[51] Int. Cl.$^5$ ........................... A61F 5/44; A61F 6/04
[52] U.S. Cl. ...................................... 604/349; 128/844
[58] Field of Search ................. 604/349; 128/842, 844

[56] References Cited

U.S. PATENT DOCUMENTS

| Re. 33,206 | 5/1990 | Conway et al. | 604/349 |
| 2,348,773 | 5/1944 | Wyman | 128/844 |
| 2,358,440 | 9/1944 | Bowman | 128/844 |
| 4,187,851 | 2/1980 | Hauser . | |
| 4,475,910 | 10/1984 | Conway et al. | 604/349 |
| 4,540,409 | 9/1985 | Nystrom et al. | 604/349 |
| 4,869,723 | 9/1989 | Harmon | 604/349 |
| 4,885,049 | 12/1989 | Johannesson | 604/349 X |
| 4,894,059 | 1/1990 | Larsen et al. | 604/349 |

FOREIGN PATENT DOCUMENTS

| 0260025 | 3/1988 | European Pat. Off. | 604/349 |
| 0325902 | 8/1989 | European Pat. Off. | 604/349 |
| 1591685 | 6/1970 | France . | |
| WO86/00816 | 2/1986 | PCT Int'l Appl. . | |
| WO87/01582 | 3/1987 | PCT Int'l Appl. . | |

Primary Examiner—Ronald Frinks
Assistant Examiner—R. Clarke
Attorney, Agent, or Firm—Ostrolenk, Faber, Gerb & Soffen

[57] ABSTRACT

The neck portion (3) of an external male urinary catheter has increased wall thickness and rigidity and comprises a first part (3a) having a maximum diameter corresponding to that of the catheter body portion (1) and a second part (3b) joining a drainage tube.

Between the first and second parts of the neck portion (3) a constriction (5) is formed having axial and radial dimensions to receive and retain the catheter body portion in a rolled-up condition.

The second part (3b) of neck portion provides a bulbous surge chamber to prevent kinking of the drainage tube and back-flow of urine.

4 Claims, 3 Drawing Sheets

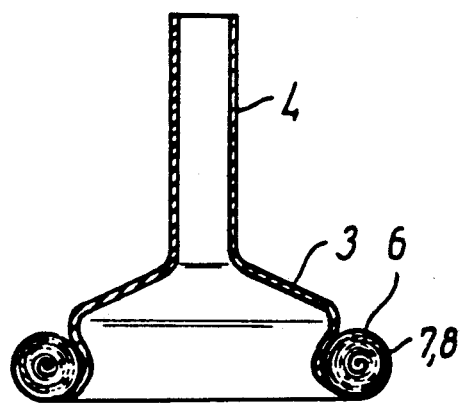
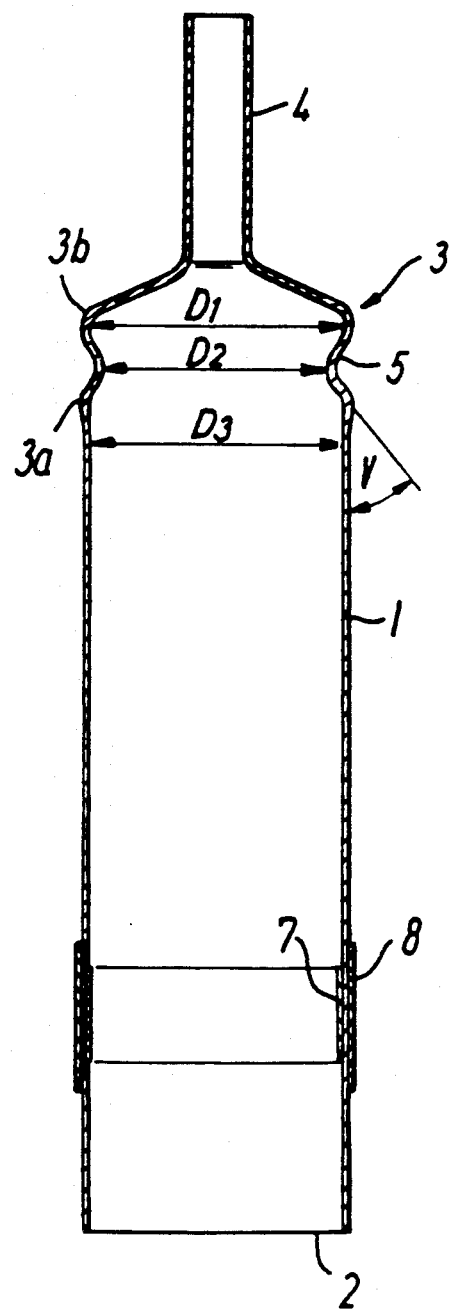

EXTERNAL MALE URINARY CATHETER AND METHOD AND APPARATUS FOR MANUFACTURING SUCH A CATHETER

This invention relates to an external male urinary catheter comprising a soft thin-walled substantially cylindrical body portion, which is open at one end and merges at the other end into a neck portion of increased wall thickness and rigidity compared to the body portion said neck portion comprising a first part having a maximum diameter corresponding to that of the body portion and a second part joining a narrow drainage tube to be connected to a urine collection bag.

Catheters of this kind are designed to be arranged as a condom on a penis in order to act as an aid against male urinary incontinence in a safe manner free of leakage and with the fewest possible inconveniences to the users, who may be fysically handicapped or elderly persons for whom greater openness concerning problems of incontinence has led to a growing demand for such aids. Whereas in the past special adhesive linings was often used to securely fasten the catheter to the normal flaccid penis, as known e.g. from U.S. Pat. No. 4,187,851 and GBA-2 096 901 it has become increasingly common to provide the catheter body portion with an integrated layer of a pressure-sensetive adhesive, which is either initally applied to the innerside of the body portion, as known from WO86/00816 or transferred to the inner side during unrolling of the rolled-up body portion of the catheter as known from GB-B-2 106 784. To prevent sticking together of successive windings of the rolled-up body portion the outer side thereof is protected by an adhesive release layer opposite the adhesive layer.

To facilitate application of the catheter the device is usually supplied, as mentioned above, with the catheter body portion rolled up from the open end towards the neck portion.

In prior art devices it has not been possible, however, to secure that the rolled-up catheter body part is always located at one particular position on the catheter just inside the neck portion and unavoidable variations in the location of the rolled-up portion will frequently lead the inconvenience during application that the user or a nurse assisting him must grip with the fingers on a part of the very thin-walled body portion and place it on the sensitive surface of the penis glans.

In order to avoid this inconvenience it has been suggested to use various forms of catheter applicators as known e.g. from U.S. Pat. No. 4,540,409 and EP-A-0236.458 Such accessories will, however, unavoidably increase the costs of the catheter-applicator combination to a level counteracting the intended supply of such devices as disposable articles.

In order to remedy these deficiencies of prior art products the present invention provides a catheter of the kind mentioned, which is characterized in that a constriction is formed between said first and second parts of the neck portion said constriction having axial and radial dimensions to receive and retain the catheter body portion in a rolled-up condition, the second part of the neck portion between the constriction and the drainage tube tapering towards the drainage tube from a maximum diameter exceeding the minimum diameter of the constriction to provide a bulbous surge chamber to prevent kinking of the drainage tube and back-flow of urine.

Thereby, the catheter may always be supplied to the user with the rolled-up body portion located at ecactly the same position on the neck portion of the catheter having increased wall-thicknes and regidity and so close to the drainage tube that on application the user or nurse may simply grip the drainage tube which is outside the penis itself and hold the neck portion against the penis glas, whereafter the body portion may be unrolled without any need to use a special applicator.

Additionally, the constriction provided in the neck portion allow the part of the neck portion outside the constriction to function as a bulbous surge chamber and prevent kinking of the drainage tube and back flow of urine even if the constriction separating this chamber from the catheter body portion has a greater diameter than normally used in prior devices provided with such anti-kink mechanisms and know e.g. from the above-mentioned GB-B 2 106 787 and U.S. Pat No. 4,540,409.

The invention further relates to a method for manufacturing an external catheter as defined and comprising the steps of dipping a substantially cylindrical mandrel having an outer contour corresponding to the envisaged inner contour of the catheter including the drainage tube into a liquid state rubber-based material and allowing the mandrel carrying a layer of said material to cure, said method being characterized by the use of a mandrel having a first part corresponding to the catheter body portion, a second part corresponding to the drainage tube and an intermediate part corresponding to the neck portion and having a circumferential groove and by repeated dipping and curing of said second part and said intermediate part only after an initial dipping and curing operation involving all parts of the mandrel to provide increased thickness and rigidity to said second part and said intermediate part.

Additionally, the invention relates to an apparatus for carrying out the method and comprising a mandrel including a first cylindrical mandrel part of a diameter corresponding to the inner diameter of a catheter body portion and a second cylindrical mandrel part of a substantial reduced diameter corresponding to the catheter drainage tube, said apparatus being characterized by having between said first and second mandrel parts an intermediate part in which a circumferential groove is formed, said groove having axial and radial dimensions to provide the constriction in the catheter neck portion between the body portion and the drainage tube said groove being provided between a first part of said intermediate portion having a maximum diameter corresponding to that of the first mandrel part and a second part tapering towards said second mandrel part from a maximum diameter exceeding the minimum diameter of the groove.

Figure 4:
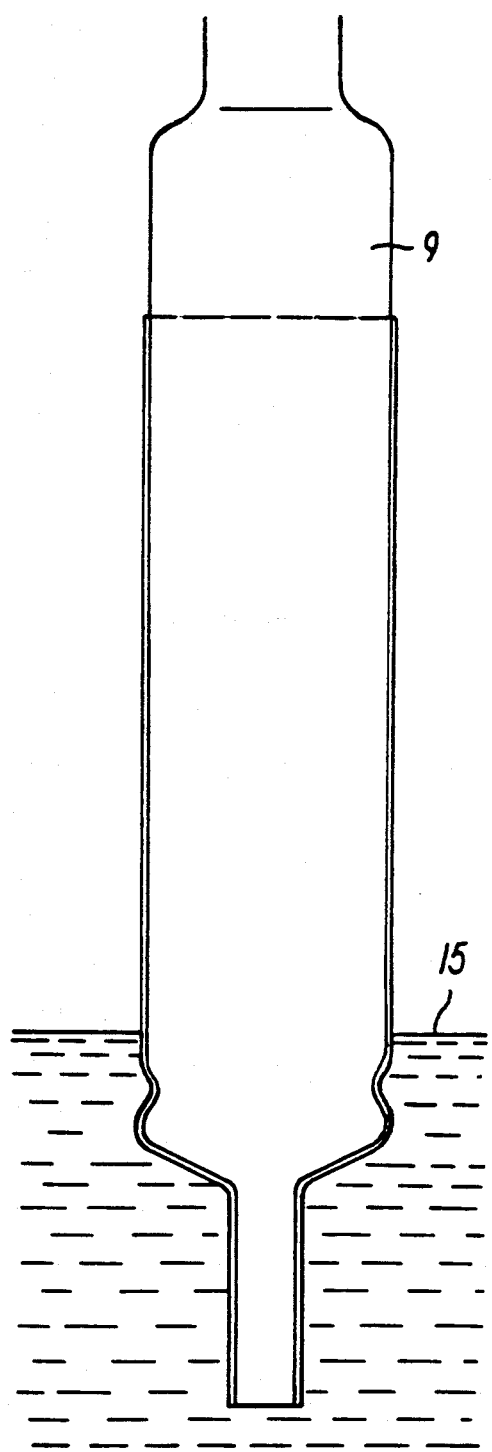
Figure 5:
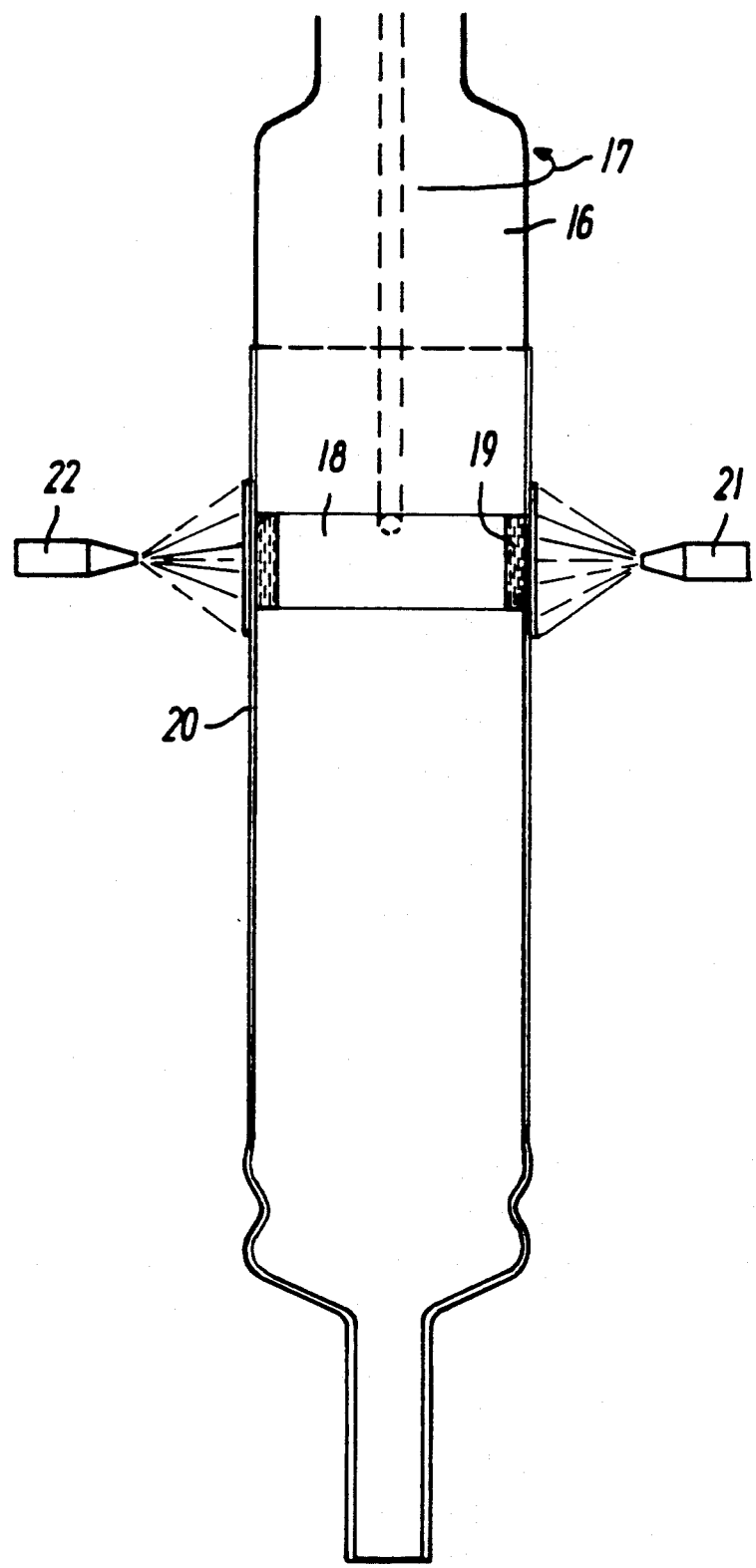

In the following, the invention will be further explained and illustrated with reference to the accompanied drawings in which FIGS. 1 and 2 are sectional views of an embodyment of an external catheter according to the invention in a rolled-up supply condition and an unrolled use condition, respectively; and FIGS. 3-5 are simplified schematic views of parts of a production apparatus for illustrating the method according to the invention.

In the embodiment shown in FIGS. 1 and 2 the external male urinary catheter according to the invention comprises a very soft, thin walled and highly flexible body portion 1 with an open end 2. At the opposite end the body portion 1 merges into a neck portion 3 having increased wall-thicknes and rigidity compared to the body portion 1.

The neck portion 3 comprises a first part 3a of a maximum inner diameter $D_3$ corresponding to the inner diameter of the body portion 1 and a second part 3b joining a narrow drainage tube 4 formed for connection to a urine collection bag, not shown, which is normally fastened to one leg of the user.

According to the invention a constriction 5 is formed between the first and second parts 3a and 3b of the neck portion 3, said constriction having acial and radial dimensions to receive and retain the body portion 1 in the rolled-up supply condition shown in FIG. 1. The second part 3b of the neck portion 3 between the constriction 5 and the drainage tube 4 tapers towards the drainage tube 4 from a maximum diameter $D_1$ exceeding the bottom diameter $D_2$ of the constriction 5 to provide a bulbous surge chamber 6 serving to prevent kinking of the drainage tube 4 and back-flow of urine, when the catheter is in use.

Whereas the diameter $D_3$ of the catheter body portion 1 and the first part 3a of the neck portion 3 may vary for adaption to different sizes of the male penis, e.g. from about 20 to about 40 mms the axial and radial dimensions of the constriction 5 serving to accomodate the rolled-up body portion will remain substantially the same regardless of the diameter of the body portion.

In preferred embodiments the minimum or bottom diameters $D_2$ of the constriction will thus be 4.5 to 6.5 mms less than the body portion diameter $D_3$ and the surface contour of the constriction 5 between the diameter $D_2$ and the diameter $D_3$ of the first part 3a of the neck portion 3 will be substantially conical with a half apex angle v of 45° to 50° with the axis of the catheter, whereas the maximum diameter $D_1$ of the second part 3b of the neck portion 3 will be 2.4 to 3.0 mms less than the diameter $D_3$ of the first portion 3a.

By these dimensions the rolled-up body portion 1 will be very safely located in the constriction 5 and on application of the catheter it will be sufficient for the user or a nurse assisting him to grip the drainage tube 4 and place the catheter in the rolled-up condition with the neck portion 3 against the penis glas and unrole the body portion 1. In particular the above-mentioned range for the angle of the conical surface contour of the constriction 5 implies that a certain slight resistance will have to be overcome before the rolled-up portion may leave the constriction 5 and reach the cylindrical body portion inside the neck portion 3.

As shown in FIG. 2 the body portion 1 may in a manner known per se from WO86/00816 be provided on part of its inner side with an integrated layer of a pressure-sensitive adhesive and on its outer side with a corresponding adhesive release layer 8 to prevent successive windings of the rolled-up body portion from sticking inseparably together.

For manufacturing the catheter a mandrel form 9 as shown in FIGS. 3 and 4 may be used. The mandrel 9 has an outer contour corresponding to the envisaged inner contour of the catheter including the drainage tube and it comprises a first cylindrical portion 10 of a diameter $D_3$ corresponding to the catheter body portion 1, a second cylindrical portion 11 of a substantially reduced diameter corresponding to the drainage tube 4 and an intermediate portion 12 in which the circumferential groove 13 is formed to provide the constriction 5 in the catheter neck portion 3. Thus the groove 13 is provided between a first part 12a of the intermediate portion 12 having the diameter $D_3$ and a second part 12b tapering towards the second mandrel portion 11 from a maximum diameter $D_2$ exceeding the minimum or bottom diameter $D_2$ of the groove 13.

In a preferred embodiment the axial and radial dimensions of the groove 13 on the mandrel 9 will correspond to the dimensions mentioned above for the constriction 5.

In a first manufacturing stage the mandrel 9 is dipped into a bath of a liquid-state rubber-material like latex as illustrated in FIG. 3 to a level 14 corresponding to the desired location of the open end 2 of the catheter to receive a layer of the liquid material to provide the soft thin-walled and flexible body portion 1.

After removal of the mandrel 9 carrying such a layer from the bath the rubber-based latex material is allowed to cure.

To obtain the increased wall thickness and regidity of the catheter drainage tube 4 and the neck portion 3 with the constriction 5 a new dipping operation is carried out, but this time only the second part 11 and the intermediate part 12 of the mandrel 9 is lowered into the bath to the level 15.

Depending on the number of succssive dipping and curing operations the thickness of the drainage tube 4 and the neck portion 3 may be adjusted to satisfied prescribed specifications.

After completion of all dipping and curing operations the catheter may now be provided with the integrated inner and outer layers 7 and 8 of a pressure-sensitive adhesive and an adhesive release agent such as silicone, respectively, by being arranged on another mandrel 16, which as shown in FIG. 5 may be supported for rotational movement in the direction of the arrow 17.

On a part of its axial length corresponding to the desirable location of the adhesive layer 7 the mandrel 16 has a circumferential depression 18 in which an insert 19 of an adhesive rejecting silicone based material is arranged.

Prior to arrangement of the pre-fabricated catheter 20 on the mandrel 16 adhesive is applied to the outer surface of the insert 19 in a liquid state, e.g. from a spraying device 21 during rotation of the mandrel 16 in the direction of the arrow 17.

Subsequently the catheter 20 is arranged for which purpose the mandrel 16 may be formed with internal ducts for supplying pressurized air to permit easy arrangement of the catheter 20 as known e.g. from WO86/00816.

With the catheter 20 subsequently arranged on the mandrel 16 the adhesive release layer 8 is applied to the outer side of the catheter to extend somewhat outside the upper and lower boundaries of the adhesive layer 7 on the inner side. The release agent may like the adhesive be supplied in a liquid stage e.g. by means of the spraying device 22 under simultaneous rotation of the mandrel 16 in the direction of the arrow 17.

Finally the catheter body portion is rolled up from the open end, whereby the adhesive layer initially applied to the insert 19 on the mandrel 16 will slip the insert 19 and stick to the inner side of the catheter, which is rolled-up until the rolled-up portion reaches the constriction 5 in the catheter neck portion.

Whereas the mandrel 16 has first and intermediate portions corresponding to the portions 10 and 12 of the mandrel 9 in FIGS. 3 and 4 it does not need having a second portion corresponding to the portion 11 of the mandrel 9.

Whereas in FIGS. 3–5 only a single mandrel is shown it will be understood that in practice a considerable number of mandrels may be supported by a common supporting member and operated simultaneously in the various manufacturing stages described above.

The constriction or external groove or channel 5 provided by the reduced diameter portion intermediate the axial length of the neck portion receives and locates the cylindrical body portion 1 in the rolled up condition and leaves a surge chamber 6 between the reduced diameter portion and the inlet to the drainage tube 4. The additional thickness of the neck portion 3 lends support for the body portion in the rolled up condition and together with the surge chamber 6 helps to prevent kinking of the drainage tube and the back-flow of urine.

I claim:

1. An external male urinary catheter comprising a soft thin-walled substantially cylindrical body portion, which is open at one end and merges at another end into a neck portion of increased wall thickness and rigidity compared to said body portion, said neck portion comprising a first part having a maximum diameter corresponding to that of the body portion and a second part joining a narrow drainage tube to be connected to a urine collection bag, wherein said neck portion includes a constriction between said first and second parts of said neck portion, said constriction having axial and radial dimensions to receive and retain the catheter body portion in a rolled-up condition, said second part of said neck portion between the constriction and the drainage tube tapering towards the drainage tube from a maximum diameter exceeding a minimum diameter of said constriction to provide a bulbous surge chamber to prevent kinking of the drainage tube and backflow of urine.

2. The external catheter of claim 1 wherein the constriction has a minimum diameter, which is 5.5 to 6.5 mms less than the diameter of said first part of the neck portion, wherein the surface contour of the constriction between its minimum diameter and the first part of the neck portion is substantially conical under a half apex angle of 45° to 50° with the axis of the cathether, and wherein said second part of the neck portion has a maximum diameter which is 2.4 to 3.0 mms less than the diameter of said first part.

3. The external catheter of claim 1 wherein part of the catheter body portion is provided on the inner side with a layer of a pressure-sensitive adhesive and on the outer side with an adhesive release layer to allow unrolling of the body portion from said rolled-up condition.

4. An external male urinary catheter comprising a soft thin-walled substantially cylindrical body portion which is open at one end and at another end merges through a neck portion to an inlet end of a drainage tube in which the neck portion is formed with a reduced diameter portion intermediate its axial length to provide an external groove or channel having axial and radial dimensions to receive, locate and retain the cylindrical body in the rolled up condition and a bulbous surge chamber between the reduced diameter portion and the inlet end of the drainage tube, said neck portion having increased wall thickness and rigidity relative to the body portion, to provide support for the rolled up body portion when received in the groove and to prevent kinking of the drainage tube.

* * * * *